United States Patent [19]

Cobb

[11] Patent Number: 4,668,835

[45] Date of Patent: May 26, 1987

[54] NOVEL TETRACYCLIC TRIENES

[75] Inventor: Raymond L. Cobb, Bartlesville, Okla.

[73] Assignee: Phillips Petroleum Co., Bartlesville, Okla.

[21] Appl. No.: 783,999

[22] Filed: Oct. 4, 1985

[51] Int. Cl.$^4$ ................................................ C07C 2/68
[52] U.S. Cl. ................................ 585/360; 570/129; 570/143; 570/183; 570/190; 585/431; 585/459; 585/472
[58] Field of Search ............... 585/410, 415, 431, 459, 585/472, 360, 361; 570/129, 130, 183, 143, 190

[56] References Cited

U.S. PATENT DOCUMENTS

| | | | |
|---|---|---|---|
| 2,526,895 | 10/1950 | Pines et al. | 585/252 |
| 3,297,673 | 1/1967 | Sellers et al. | 526/87 |
| 4,170,576 | 10/1979 | Hall et al. | 585/20 |
| 4,265,818 | 5/1981 | Wiegers et al. | 585/361 |
| 4,551,573 | 11/1985 | Cobb | 585/459 |

OTHER PUBLICATIONS

Chem. Abstracts, vol. 62, 7802h.

*Primary Examiner*—Asok Pal
*Attorney, Agent, or Firm*—Stephen E. Reiter

[57] ABSTRACT

The alkylation of para-substituted isopropyl benzenes with dipentenes employing an aluminum halide catalyst system produces novel tetracyclic compounds.

4 Claims, No Drawings

NOVEL TETRACYCLIC TRIENES

This invention relates to novel compositions of matter. In one aspect, this invention relates to tetracylic tri-unsaturated compounds. In another aspect, the present invention relates to cyclic alkylation of aromatic compounds to produce unsaturated tetracylic compounds.

BACKGROUND

The alkylation of aromatic compounds with olefins is a well known reaction. Many different substituted aromatic compounds have been prepared by the acid catalyzed reaction of olefins with aromatic compounds. It is often difficult, if not impossible, to predict the product(s) which will be obtained when a given aromatic/olefin pair are contacted under alkylation conditions in the presence of catalyst. Frequently, complex mixtures of products are obtained due to olefin isomerization, oligomerization, polycondensation reactions, etc. Especially with diolefinic compounds, it is not always possible to obtain useful yields of alkylated products.

OBJECTS OF THE INVENTION

An object of the present invention is the alkylation of aromatic compounds with the diolefin, dipentene.

Another object of the present invention is the production of novel tetracyclic compounds.

These and other objects of my invention will become more apparent from the disclosure and claims herein provided.

STATEMENT OF THE INVENTION

I have discovered that the reaction of a para-substituted isopropyl benzene with the diolefinic moiety, dipentene (or limonene) in the presence of an aluminum trihalide catalyst system, produces novel tetracyclic compounds. The novel compounds produced in accordance with the present invention are useful, for example, as fuel additives, fragrance chemicals and the like.

DETAILED DESCRIPTION OF THE INVENTION

In accordance with the present invention, 8-substituted-2,4,4,10-tetramethyltetracyclo[8.2.2$^{1,10}$,1$^{5,9}$,0$^{1,15}$]pentadeca-5,7,9-trienes, i.e., compounds having the structure:

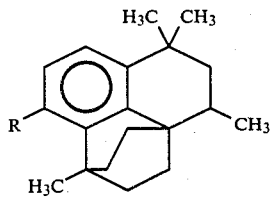

are provided. The novel compounds of the invention are prepared by contacting a para-substituted isopropyl benzene with a dipentene compound and an aluminum halide catalyst system under alkylation conditions.

The para-substituted isopropyl benzene compounds contemplated within the scope of the present invention conform to the general formula:

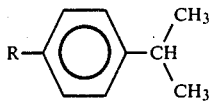

wherein R is a normal alkyl group having one to four carbon atoms or a halogen. Examples of suitable para-substituted isopropyl benzene compounds include para-cymene (para-isopropyl toluene), para-ethylisopropyl benzene, para-chloroisopropyl benzene, and the like.

The dipentene compound useful in the practice of the present invention can be represented by the cyclohexadiene structure shown below.

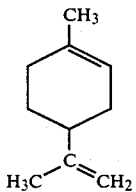

This structure includes the pure d or l forms, i.e., d- or l-limonene, as well as d,l mixtures, common referred to as dipentene.

The catalyst employed in the practice of the present invention is an aluminum halide catalyst system. The designation "aluminum halide catalyst system" is intended to refer to aluminum halide alone, as well as the presently preferred aluminum halide-elemental iodine combination. The aluminum halide component can be represented as $$AlX_3$$

wherein each X is independently selected from the halogens. Thus, suitable aluminum halide compounds include aluminum tribromide ($AlBr_3$), dichloroaluminum bromide ($AlCl_2Br$), dibromoaluminum fluoride ($AlBr_2F$), aluminum tritriiodide ($AlI_3$), aluminum chloride ($AlCl_3$) and the like and mixtures of any two or more thereof. Aluminum chloride is the presently preferred aluminum halide because it is readily available and provides a selective as well as a reactive catalyst.

When mixed catalyst is employed, the catalyst components, i.e. $AlX_3$ and $I_2$, can be combined in any suitable ratio as can be readily determined by one skilled in the art. For purposes of guidance, it is suggested that a weight ratio of $I_2:AlX_3$ in the range of about 0.01:1 up to 1:1 be employed. It is preferred, for most efficient use of reagents and for optimum catalyst performance, that a weight ratio of $I_2:AlX_3$ in the range of about 0.1:1 up to 0.4:1 be employed.

The catalyst components can be combined in any suitable manner as can be readily determined by those skilled in the art. Thus, catalyst components can be dry mixed, slurried in a solvent which is not reactive under the reaction conditions employed, slurried in the reactant aromatic compound, slurried in an aliquot of the alkylated aromatic product or combined by other suitable techniques.

Although the catalyst can withstand the presence of small amounts of moisture, it is preferred that care be taken to exclude the presence of moisture from the reaction medium. While optional, it is preferred that catalyst preparation as well as the alkylation reaction be carried out in an inert atmosphere, i.e., in the presence of a gas such as $N_2$, Ar and the like.

REACTION CONDITIONS

The molar ratio of olefinic compound to aromatic compound employed in the practice of the invention can vary broadly. In order to provide further guidance, it is suggested that a molar ratio of olefinic compound to aromatic compound of at least about 0.05:1 up to about 5:1 be employed. Ratios below the lower value provide low product yield based on the amount of starting material employed, while ratios above the upper value have a tendency to produce undesirable levels of by-products due to multiple alkylation reactions of the aromatic ring, olefin rearrangement and oligomerization, and the like. Ratios in the range of about 0.2:1 up to 3:1 are preferred for efficient use of starting materials and minimum formation of by-products, which in turn simplifies the task of product recovery.

The alkylation reaction of the invention can be carried out in any suitable vessel which provides efficient contacting between the catalyst components and the reactants. For simplicity, a stirred batch reactor can be employed. The material of construction of the reaction vessel should be chosen so as to be resistant to the possibly corrosive nature of the catalyst. Thus, a glass-lined vessel, Hastelloy C or other resistant alloys as are known in the art are suitable. The major requirement which any reaction vessel must satisfy is the ability to provide rapid, efficient mixing since the alkylation reaction of the invention, especially when catalyzed by $AlX_3$—$I_2$, is frequently a very rapid reaction.

The molar ratio of $AlX_3$ to reactant aromatic compound can be readily determined by those skilled in the art. In order to provide further guidance, it is suggested that a molar ratio of at least about 0.001 moles of $AlX_3$ per mole of reactant aromatic compound up to a molar ratio of about 1:1 be employed. Preferably, a molar ratio in the range of about 0.01:1 up to 0.5:1 will be employed for most efficient utilization of reagents.

Because the alkylation reaction carried out according to the invention is generally quite rapid, temperature requirements for the alkylation reaction are quite modest. Broadly, a temperature range of about 20° to about 80° C. is appropriate. The preferred temperature range for cyclialkylation is about 30° to about 65° C.

It is convenient as a means of temperature control to employ excess reactant aromatic compound or alkylated aromatic product or other diluents which are relatively inert to the reaction conditions employed. When the desired alkylation reaction is rapid and consequently required contact between catalyst and diluent is short, the stability of the diluent under the reaction conditions employed is not as critical as when longer reaction times are employed. In order to minimize by-product formation, however, it is preferred that diluents which do not undergo substantial isomerization, rearrangement, degradation or the like under the reaction conditions be employed. It is especially preferred to use alkylated aromatic product as the diluent for ease of product recovery.

The pressure at which reaction is carried out is not critical. If reaction is carried out in a sealed vessel, autogeneous pressure is suitable, although higher or lower pressures can be employed. Reaction can also be carried out at atmospheric pressure in an open reaction vessel, in which case the vessel will preferably be equipped with a moisture trap to prevent significant exposure of catalyst to moisture.

Reaction time is generally quite short and is often dictated by the type of equipment employed. Sufficient time must be provided for thorough contacting of the aromatic compound, the olefinic compound and the catalyst. Although in theory there is no upper limit as to the reaction time which may be employed, reaction is generally quenched shortly after all reagents are contacted to prevent a significant degree of side reactions from occurring. Thus, depending on the type of reaction vessel employed and its stirring capabilities, etc., reaction time could be a matter of seconds to a matter of minutes. Reaction is then quenched and worked up as described in more detail below to prevent a significant degree of product isomerization or degradation from occurring in the continued presence of active catalyst.

PRODUCT RECOVERY

To quench the alkylation reaction, the mixture is poured into water, preferably ice water. After phase separation, the organic layer can be washed additional times with water if desired to aid removal of aluminum halide catalyst. One or more such additional washings can be carried out with dilute alkali solution to further aid aluminum halide removal. Additional washing of the organic layer, as desired, can be carried out with dilute sodium thiosulfate solution to aid removal of residual $I_2$ from the aqueous phase. Pure product is then typically recovered by reduced pressure fractional distillation of the washed reaction mixture.

EXAMPLES

All of the experiments described below were carried out in conventional laboratory glassware equipped with a mechanical stirrer and a nitrogen bubbler to prevent introduction of moisture into the reaction vessel. A quantity of para-cymene and catalyst was placed in the reaction vessel, stirring commenced, then a quantity of olefin (dipentene, limonene or α-pinene) added dropwise over about 5–10 minutes. Reaction temperature was maintained at the desired level until about 15 minutes had elapsed from the time olefin addition had started, then a sample was withdrawn for analysis.

Analyses were done by gas liquid chromatography (glc) employing either a 10 foot by ⅛ inch column packed with 5 wt. % SP 1200 and 1.75 wt % Bentone 34 on Supelcoport, a low polarity ester; supplied by Supelco, Inc., Supelco Park, Bellefonte, PA 16823, or a 50 meter capillary column coated with OV 101 silicone fluid; supplied by Ohio Valley Specialty Chemicals, Inc., 115 Industry Rd., Marietta, OH 45750. Analyses on the former column were carried out using a temperature program of 10° C./minute from a starting temperature of 150° C. up to 200° C. Analyses on the latter column were carried out from 50° C. to 250° using a temperature program of 10° C./min.

Reagents charged, reaction conditions employed and analytical results are summarized in Table I which follows.

TABLE I

| | Reagent, mL | | | Reaction Conditions | | Analyses | |
|---|---|---|---|---|---|---|---|
| Run | p-Cymene | Olefin* | Catalyst | Solvent, mL | Temp. °C. | P-Cymene Conversion, % | Selectivity to Tetracyclic Prod., % |
| 1 | 150 | DP, 100 | Filtrol 13,25 | None | 155 | 32 | trace |
| 2 | 150 | DP, 100 | 96% H$_2$SO$_4$, 50 | None | 30 | 46 | trace |
| 3 | 150 | 100 | 15 g AlCl$_3$; 4 g I$_2$ | None | 40 | 29 | trace |
| 4 | 150 | DP, 100 | 15 g AlCl$_3$ | None | 35 | 12 | 11 |
| 5 | 150 | DP, 100 | 15 g AlCl$_3$; 4 g I$_2$ | None | 35 | 24 | 46 |
| 6 | 175 | DP, 100 | 15 g AlCl$_3$; 4 g I$_2$ | PMI**,25 | 65 | 22 | 43 |
| 7 | 150 | L, 100 | 10 g AlCl$_3$ | None | 40 | 21 | 5 |
| 8 | 100 | L, 100 | 10 g AlCl$_3$; 3 g I$_2$ | None | 35 | 15 | 14 |
| 9 | 175 | L, 100 | 15 g AlCl$_3$; 4 g I$_2$ | None | 38 | 11 | 23 |

*DP = dipentene
P = pinene
L = limonene
**PMI = pentamethylindane

The results presented in the Table demonstrate that the novel tetracyclic compound of the invention is obtained when para-cymene and dipentene or limonene are contacted in the presence of AlCl$_3$ alone or AlCl$_3$-I$_2$. Essentially none of the novel tetracyclic compound is obtained when other catalysts such as Filtrol 13 (an acid clay) or concentrated sulfuric acid are employed as catalysts. Similarly, an olefin isomeric with dipentene and limonene, i.e., pinene, did not undergo comparable cyclialkylation to produce the title tetracyclic compound.

The results in Table I suggest that the preferred catalyst is the AlCl$_3$-I$_2$ combination and that dipentene is the preferred olefin for use in preparing the title tetracyclic olefin.

The reaction mixtures from several invention runs were combined and fractionally distilled in vacuo. Once unreacted starting materials were removed overhead, the undistilled fraction was recrystallized from heptane, giving white prisms which melted at 126°–128° C. Mass spectral analysis of the sample gave a parent peak at mass 268, which is consistent with a compound having the empirical formula C$_{20}$H$_{28}$. The named structure was also confirmed by proton and C nuclear magnetic resonance analysis.

The examples have been provided merely to illustrate the practice of my invention and should not be read so as to limit the scope of my invention or the appended claims in any way. Reasonable variations and modifications, not departing from the essence and spirit of my invention, are contemplated to be within the scope of patent protection desired and sought.

I claim:

1. A novel composition of matter comprising 8-R-2,4,4,10-tetramethyltetracyclo[8.2.2$^{1,10}$,1$^{5,9}$,0$^{1,15}$]pentadeca-5,7,9-triene, wherein R is a C$_1$ to C$_4$ normal alkyl radical or a halogen.

2. A composition of matter in accordance with claim 1 wherein R is methyl.

3. A method for producing 8-R-2,4,4,10-tetramethyltetracyclo[8.2.2$^{1,10}$,1$^{5,9}$,0$^{1,15}$]pentadeca-5,7,9-trienes, wherein R is a C$_1$ to C$_4$ normal alkyl radical or a halogen, which comprises contacting an aromatic compound having the structure:

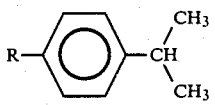

wherein R is as defined above, with a diolefinic compound having the structure:

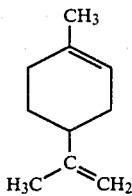

under alkylation conditions in the presence of a catalyst system comprising:

AlX$_3$ wherein X is a halogen.

4. A method in accordance with claim 3 wherein said catalyst system further comprises:

I$_2$;

wherein the weight ratio of I$_2$ to AlX$_3$ is in the range of about 0.01 to 1:1.

* * * * *